US011304636B2

(12) United States Patent
Hu et al.

(10) Patent No.: US 11,304,636 B2
(45) Date of Patent: Apr. 19, 2022

(54) OXIMETER

(71) Applicant: CONTEC MEDICAL SYSTEMS CO., LTD., Qinhuangdao (CN)

(72) Inventors: Kun Hu, Qinhuangdao (CN); Yunlong Xu, Qinhuangdao (CN); Jinling Zhang, Qinhuangdao (CN); Yatao Zhao, Qinhuangdao (CN); Zhichao Song, Qinhuangdao (CN); Di Wu, Qinhuangdao (CN); Bohua Yan, Qinhuangdao (CN)

(73) Assignee: CONTEC MEDICAL SYSTEMS CO., LTD., Hebei (CN)

( * ) Notice: Subject to any disclaimer, the term of this patent is extended or adjusted under 35 U.S.C. 154(b) by 112 days.

(21) Appl. No.: 16/755,037

(22) PCT Filed: Aug. 15, 2019

(86) PCT No.: PCT/CN2019/100795
§ 371 (c)(1),
(2) Date: Apr. 9, 2020

(87) PCT Pub. No.: WO2020/035025
PCT Pub. Date: Feb. 20, 2020

(65) Prior Publication Data
US 2020/0261004 A1  Aug. 20, 2020
US 2021/0251537 A9  Aug. 19, 2021

(30) Foreign Application Priority Data

Aug. 16, 2018  (CN) .......................... 201810932722.9

(51) Int. Cl.
*A61B 5/1455* (2006.01)
*A61B 5/00* (2006.01)

(52) U.S. Cl.
CPC ........ *A61B 5/14552* (2013.01); *A61B 5/6824* (2013.01); *A61B 5/6826* (2013.01);
(Continued)

(58) Field of Classification Search
CPC .............. A61B 5/1455; A61B 5/14551; A61B 5/14552; A61B 5/6826; A61B 5/6838;
(Continued)

(56) References Cited

U.S. PATENT DOCUMENTS 9,398,870 B2 *  7/2016  Bechtel ................. A61B 5/742
9,579,039 B2 *  2/2017  Jansen ............... A61B 5/14542

* cited by examiner

*Primary Examiner* — Eric F Winakur
(74) *Attorney, Agent, or Firm* — Armstrong Teasdale LLP

(57) ABSTRACT

Embodiments of the disclosure provide an oximeter, including a blood oxygen collecting unit that has a first light emitting unit, a second light emitting unit, and a light receiving sensor, the first light emitting unit emitting a red light, the second light emitting unit emitting an infrared light, and the light receiving sensor receiving the red light emitted by the first light emitting unit and the infrared light emitted by the second light emitting unit and not absorbed by the human body, and converting them into an electrical signal, a storage unit that stores a first threshold value, a microprocessor that calculates a blood oxygen saturation of the human body based on the electrical signal detected by the light receiving sensor, and includes a judging unit that judges whether the blood oxygen saturation is lower than the first threshold value, and a display unit.

14 Claims, 3 Drawing Sheets

(52) U.S. Cl.
CPC .......... *A61B 5/6838* (2013.01); *A61B 5/7235* (2013.01); *A61B 5/742* (2013.01); *A61B 5/746* (2013.01)

(58) Field of Classification Search
CPC ..... A61B 5/7235; A61B 5/7282; A61B 5/742; A61B 5/746
See application file for complete search history.

OXIMETER

CROSS REFERENCE TO RELATED APPLICATIONS

This patent application is a National Stage Entry of PCT/CN2019/100795 filed on Aug. 15, 2019, which claims the benefit and priority of Chinese Patent Application No. 201810932722.9 filed on Aug. 16, 2018, the disclosures of which are incorporated by reference herein in their entirety as part of the present application.

BACKGROUND

Embodiments of the present disclosure relate to an oximeter, and particularly to an oximeter that performs a flickering alarm at a low blood oxygen saturation.

Oximeter is used to detect the blood oxygen saturation of a human body, and the blood oxygen saturation is one of the important physiological parameters reflecting human body health. More and more patients are measuring their health status by monitoring blood oxygen saturation.

In the prior art, when it is detected that the blood oxygen saturation is lower than a threshold value, the patient or the medical staff is usually alerted by vibration stimulation or sound stimulation, and the user may also be alerted by visual stimulation.

Specifically, Patent Document 1 (CN201720778672.4) relates to a mobile communication terminal. When the blood oxygen saturation of a human body is lower than a preset value, an alarm device issues an alarm and a warning lamp flickers.

Patent Document 2 (CN201320543579.7) relates to a palm-type pulse oximeter which is made to have a function of prompt tone for measured abnormal values by setting a buzzer. At the same time, an indicator lamp is added to realize a flickering indication function for abnormal values.

Patent Document 3 (CN201120199935.9) relates to an oximeter, in which a control unit controls a display means to display measurement values in different ranges in different colors based on judgment result of a judging unit. In Patent Document 3, the measurement results may be marked or prompted, so that the surveyor can intuitively and clearly know whether his/her blood oxygen saturation is normal or not, which improves the user experience of the oximeter.

BRIEF DESCRIPTION

Inventor of the present disclosure finds out that the above-mentioned prior art has the following problems.

Patent Documents 1 and 2 both alert the user by adding an alarm, a buzzer, or an indicator lamp, increasing the cost of the equipment. Patent Document 3 only issues a warning by color change of the measurement parameters, and the warning effect is not obvious enough.

In view of the above-mentioned shortcomings of the prior art, the present disclosure provides an oximeter that performs a flickering alarm at a low blood oxygen saturation, and specifically, provides the following technical solution.

An oximeter is provided, including a blood oxygen collecting unit that has a first light emitting unit, a second light emitting unit, and a light receiving sensor, the first light emitting unit emitting a red light, the second light emitting unit emitting an infrared light, and the light receiving sensor receiving the red light emitted by the first light emitting unit and not absorbed by a human body and the infrared light emitted by the second light emitting unit and not absorbed by the human body, and converting them into an electrical signal, a storage unit that stores a first threshold value, a microprocessor that calculates a blood oxygen saturation of the human body based on the electrical signal detected by the light receiving sensor, and includes a judging unit that judges whether the blood oxygen saturation is lower than the first threshold value, and a display unit that, in a case where the judging unit judges that the blood oxygen saturation is lower than the first threshold value, flickeringly displays the blood oxygen saturation at a first frequency.

The oximeter of the present disclosure, which alerts the user by flickeringly displaying the blood oxygen saturation at a predetermined frequency, may significantly improve the warning effect without increasing the equipment cost. In addition, visual stimulation is suitable for patients with hearing impairments, and it is also suitable for noisy environments. At the same time, sound-free prompts would not affect other people's rest, life, or work.

Alternatively, the storage unit further stores a second threshold value smaller than the first threshold value. The judging unit, in a case where it is judged that the blood oxygen saturation is lower than the first threshold value, judges whether the blood oxygen saturation is lower than the second threshold value. The display unit, in a case where the judging unit judges that the blood oxygen saturation is lower than the second threshold value, flickeringly displays the blood oxygen saturation at a second frequency greater than the first frequency.

Alternatively, the storage unit further stores a third threshold value smaller than the second threshold value. The judging unit, in a case where it is judged that the blood oxygen saturation is lower than the second threshold value, judges whether the blood oxygen saturation is lower than the third threshold value. The display unit, in a case where the judging unit judges that the blood oxygen saturation is lower than the third threshold value, flickeringly displays the blood oxygen saturation at a third frequency greater than the second frequency.

Alternatively, the storage unit further stores a first duration. The judging unit, in a case where it is judged that the blood oxygen saturation is lower than the first threshold value, judges whether a duration in this case exceeds the first duration. The display unit, in a case where the judging unit judges that the blood oxygen saturation is lower than the first threshold value and it continues for the first duration, flickeringly displays the blood oxygen saturation at the first frequency.

Alternatively, the storage unit further stores a second duration smaller than or equal to the first duration. The judging unit, in a case where it is judged that the blood oxygen saturation is lower than the second threshold value, judges whether a duration in this case exceeds the second duration. The display unit, in a case where the judging unit judges that the blood oxygen saturation is lower than the second threshold value and it continues for the second duration, flickeringly displays the blood oxygen saturation at the second frequency.

Alternatively, the storage unit further stores a third duration smaller than or equal to the second duration. The judging unit, in a case where it is judged that the blood oxygen saturation is lower than the third threshold value, judges whether a duration in this case exceeds the third duration. The display unit, in a case where the judging unit judges that the blood oxygen saturation is lower than the third threshold value and it continues for the third duration, flickeringly displays the blood oxygen saturation at the third frequency.

Alternatively, the oximeter further includes an input unit for setting at least one of the first threshold value, the second threshold value, the third threshold value, the first frequency, the second frequency, the third frequency, the first duration, the second duration, and the third duration.

Alternatively, the oximeter further includes an I/O interface for charging the battery unit and/or connecting to other blood oxygen collecting devices.

Alternatively, the oximeter further includes a wireless communication unit.

Alternatively, the oximeter is a finger clip oximeter, a wrist oximeter, or a head-mounted oximeter. A blood oxygen collecting unit of the finger clip oximeter includes a concave blood oxygen collecting port in which a finger can be put. The first light emitting unit, the second light emitting unit, and the light receiving sensor are set in the concave blood oxygen collecting port. A blood oxygen collecting unit of the wrist oximeter includes a blood oxygen finger clip set outside a casing, and the blood oxygen finger clip is connected with an interface set at the casing.

The oximeter according to the present disclosure, in which the lower the blood oxygen saturation is, the higher the flickering frequency is, thus can further improve the warning effect in an emergency situation.

BRIEF DESCRIPTION OF THE DRAWINGS

In order to describe the technical solutions of the embodiments of the present disclosure more clearly, drawings of the embodiments will be briefly described below. Obviously, the drawings described below merely relate to some embodiments of the present disclosure, other than restrictions to the present disclosure.

DETAILED DESCRIPTION

In order to clarify the technical solution and advantages of the embodiments of the present disclosure, the technical solutions of the embodiments of the present disclosure will be clearly and completely described in conjunction with the drawings of the embodiments of the present disclosure below. Obviously, the embodiments to be described refer to a part of the embodiments of the present disclosure, other than all of the embodiments. On the basis of the embodiments of the present disclosure to be described, all other embodiments those skilled in the art obtain requiring no inventive effort also belong to the scope protected by the present disclosure.

Figure 1:
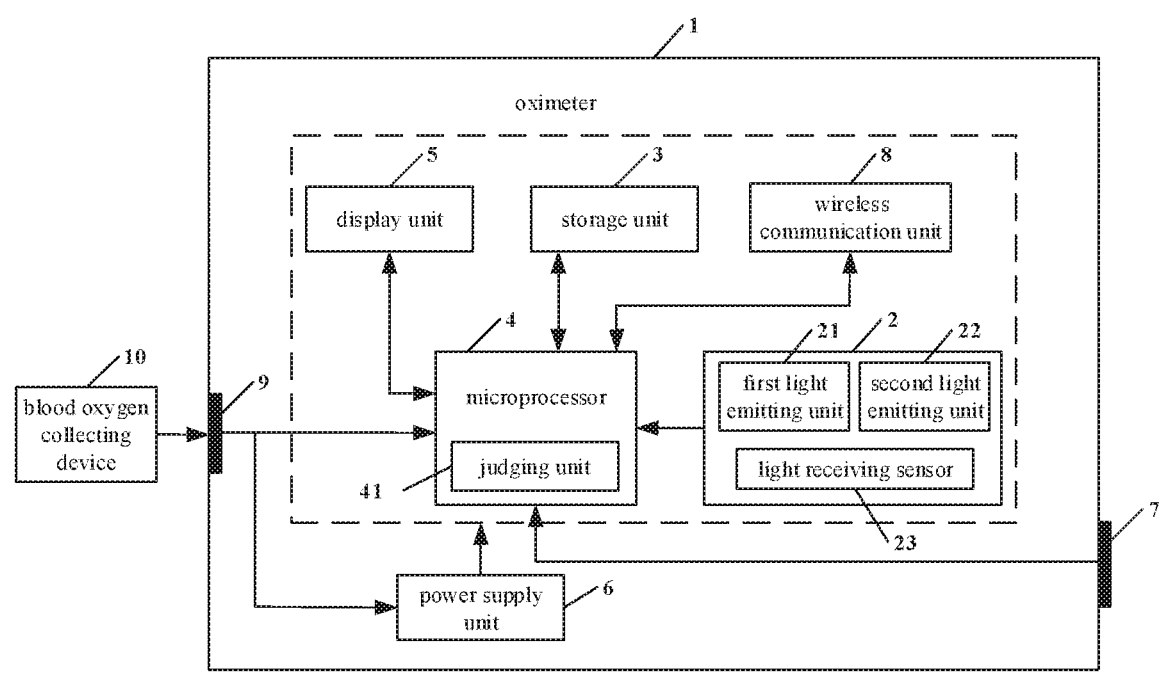
FIG. 1 is a schematic structural diagram of an oximeter according to an embodiment of the present disclosure.

FIG. 1 is a schematic structural diagram of an oximeter according to an embodiment of the present disclosure.

As shown in FIG. 1, the oximeter 1 of the present embodiment includes a blood oxygen collecting unit 2 that has a first light emitting unit 21, a second light emitting unit 22, and a light receiving sensor 23, the first light emitting unit 21 emitting a red light, the second light 22 emitting unit emitting an infrared light, and the light receiving sensor 23 receiving the red light emitted by the first light emitting unit 21 and not absorbed by a human body and the infrared light emitted by the second light emitting unit 22 and not absorbed by the human body, and converting them into an electrical signal, a storage unit 3 that stores a first threshold value, a microprocessor 4 that calculates a blood oxygen saturation of the human body based on the electrical signal detected by the light receiving sensor 23, and includes a judging unit 41 that judges whether the blood oxygen saturation is lower than the first threshold value, and a display unit 5 that, in a case where the judging unit 41 judges that the blood oxygen saturation is lower than the first threshold value, flickeringly displays the blood oxygen saturation at a first frequency.

The oximeter 1 of the present embodiment may be a portable oximeter such as a finger clip oximeter, a wrist oximeter, or a head-mounted oximeter well-known in the art, and it may further be a table oximeter used in hospital, and the present disclosure has no limitation on this.

The blood oxygen collecting unit 2 of the present embodiment has a first light emitting unit 21, a second light emitting unit 22, and a light receiving sensor 23. The first light emitting unit 21 and the second light emitting unit 22 are, for instance, LEDs, which are light emitting diodes. The first light emitting unit 21 emits a red light of 660 nm for instance, and the second light emitting unit 22 emits an infrared light of 905 nm, 910 nm, or 940 nm for instance. The light receiving sensor 23 is, for instance, a photosensitive sensor, receiving lights emitted by the first light emitting unit 21 and the second light emitting unit 22 and not absorbed by the human body, and converting them into an electrical signal.

In a specific working process, the first light emitting unit 21 and the second light emitting unit 22 may alternately emit light. In this way, the light receiving sensor 23 can alternately receive the red light emitted by the first light emitting unit 21 and not absorbed by the human body and the infrared light emitted by the second light emitting unit 22 and not absorbed by the human body. In addition, the light receiving sensor 23 may include two sensors, each of which independently receives the lights emitted by the first light emitting unit 21 and the second light emitting unit 22 and not absorbed by the human body. In this way, the first light emitting unit 21 and the second light emitting unit 22 do not need to emit light alternately, but may emit light continuously.

Furthermore, the blood oxygen collecting unit 2 may also include three or more light emitting units to improve the collection accuracy.

In a case where the oximeter 1 is a finger clip oximeter, a blood oxygen collecting unit 2 includes a concave blood oxygen collecting port in which a finger can be put, and the first light emitting unit 21, the second light emitting unit 22, and the light receiving sensor 23 are set in the concave blood oxygen collecting port.

In a case where the oximeter 1 is a wrist oximeter, a blood oxygen collecting unit 2 includes a blood oxygen finger clip set outside a casing, and the blood oxygen finger clip is connected with an interface set at the casing. In addition, the blood oxygen collecting unit 2 of the wrist oximeter may also be set inside the casing.

Figure 4:
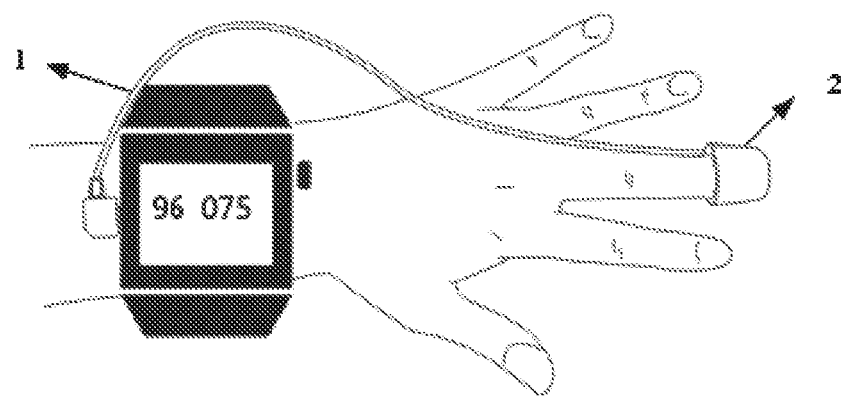
FIG. 4 is an example of a wrist oximeter according to an embodiment of the present disclosure.

Specifically, FIG. 4 is an example of a wrist oximeter according to an embodiment of the present disclosure. As shown in FIG. 4, the blood oxygen collecting unit 2 of the wrist oximeter, i.e., a blood oxygen finger clip, is set outside, and the blood oxygen finger clip is set to be connected with an interface of the casing.

In a case where the oximeter 1 is a head-mounted oximeter, a blood oxygen collecting unit 2 may be set outside or inside the casing like a wrist oximeter. When set outside, the blood oxygen collecting unit 2 is connected through an interface set on the casing.

The blood oxygen collecting unit 2 sends the collected electrical signal to the microprocessor 4 which calculates the blood oxygen saturation of the human body based on the received electrical signal. The method for the microprocessor 4 to calculate the blood oxygen saturation based on the electrical signal collected by the blood oxygen collecting unit 2 may be any method known in the art, and is not described in detail in the present disclosure.

The microprocessor 4 includes a judging unit 41 that judges whether the calculated blood oxygen saturation is lower than a first threshold value stored in the storage unit 3.

The display unit 5, in a case where the judging unit 41 judges that the blood oxygen saturation is lower than the first threshold value, flickeringly displays the blood oxygen saturation at the first frequency. Any one or more of a bar graph, a blood oxygen value, a pulse rate value, a PI value, and a waveform graph can be displayed on the display unit 5 of the present embodiment, and the present disclosure has no limitation on this.

Figure 2:
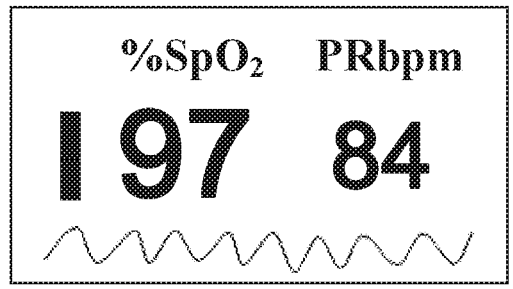
FIG. 2 is an example of a screen displayed by a display unit of an oximeter according to an embodiment of the present disclosure.
Figure 3:
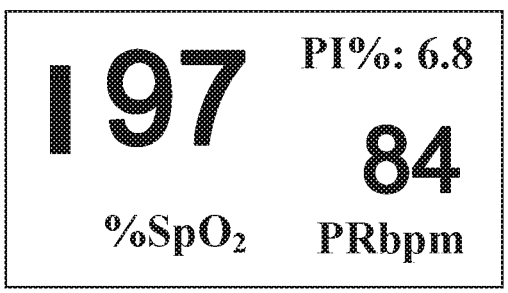
FIG. 3 is another example of a screen displayed by a display unit of an oximeter according to an embodiment of the present disclosure.

Specifically, FIG. 2 is an example of a screen displayed by a display unit of an oximeter according to an embodiment of the present disclosure. FIG. 3 is another example of a screen displayed by a display unit of an oximeter according to an embodiment of the present disclosure. As shown in FIG. 2, a bar graph, a blood oxygen value, a pulse rate value, and a waveform graph are displayed on the display unit 5. As shown in FIG. 3, a bar graph, a blood oxygen value, a pulse rate value, and a PI value are displayed on the display unit 5.

In the present embodiment, the display unit 5 may flickeringly display the blood oxygen saturation. In addition, the entire screen of the display unit 5 may be flickeringly displayed, or the blood oxygen saturation and other parameter values may be alternately flickeringly displayed to alert the user.

The oximeter 1 according to the present embodiment, which alerts the user by flickeringly displaying the blood oxygen saturation at a first frequency, may significantly improve the warning effect without increasing the equipment cost. In addition, visual stimulation is suitable for patients with hearing impairments, and it is also suitable for noisy environments. At the same time, sound-free prompts would not affect other people's rest, life, or work.

Alternatively, the storage unit further stores a second threshold value smaller than the first threshold value. The judging unit, in a case where it is judged that the blood oxygen saturation is lower than the first threshold value, judges whether the blood oxygen saturation is lower than the second threshold value. The display unit, in a case where the judging unit judges that the blood oxygen saturation is lower than the second threshold value, flickeringly displays the blood oxygen saturation at a second frequency greater than the first frequency.

Alternatively, the storage unit further stores a third threshold value smaller than the second threshold value. The judging unit, in a case where it is judged that the blood oxygen saturation is lower than the second threshold value, judges whether the blood oxygen saturation is lower than the third threshold value. The display unit, in a case where the judging unit judges that the blood oxygen saturation is lower than the third threshold value, flickeringly displays the blood oxygen saturation at a third frequency greater than the second frequency.

Alternatively, the storage unit further stores a first duration. The judging unit, in a case where it is judged that the blood oxygen saturation is lower than the first threshold value, judges whether a duration in this case exceeds the first duration. The display unit, in a case where the judging unit judges that the blood oxygen saturation is lower than the first threshold value and it continues for the first duration, flickeringly displays the blood oxygen saturation at the first frequency.

Alternatively, the storage unit further stores a second duration smaller than or equal to the first duration. The judging unit, in a case where it is judged that the blood oxygen saturation is lower than the second threshold value, judges whether a duration in this case exceeds the second duration. The display unit, in a case where the judging unit judges that the blood oxygen saturation is lower than the second threshold value and it continues for the second duration, flickeringly displays the blood oxygen saturation at the second frequency.

Alternatively, the storage unit further stores a third duration smaller than or equal to the second duration. The judging unit, in a case where it is judged that the blood oxygen saturation is lower than the third threshold value, judges whether a duration in this case exceeds the third duration. The display unit, in a case where the judging unit judges that the blood oxygen saturation is lower than the third threshold value and it continues for the third duration, flickeringly displays the blood oxygen saturation at the third frequency.

The above embodiment will be described with a specific example below.

Example 1

The first threshold value is 90%, the second threshold value is 85%, and the third threshold value is 80%. When the real-time monitored blood oxygen saturation is greater than or equal to 90%, no action is triggered; when it is lower than 90% and lasts for 10 seconds within this range (which means, the first duration is 10 seconds), the display parameter (i.e., the blood oxygen saturation) in the display screen of the display module flickers at a frequency of 0.5 times/second (i.e., at the first frequency); when it is lower than 85% and lasts for 9 seconds within this range (which means, the second duration is 9 seconds), the display parameter flickers at a frequency of 1 time/second (i.e., at the second frequency); and when it is lower than 80% and lasts for 8 seconds within this range (which means, the third duration is 8 seconds), the display parameter flickers at a frequency of 2 times/second (i.e., at the third frequency).

Specifically, it is shown in Table 1 below.

TABLE 1

| | threshold value | duration | frequency |
| --- | --- | --- | --- |
| first | 90% | 10 seconds | 0.5 times/second |
| second | 85% | 9 seconds | 1 time/second |
| third | 80% | 8 seconds | 2 times/second |

In the oximeter of the above embodiment of the present disclosure, the lower the blood oxygen saturation is, the shorter the waiting time for flickering is, and the higher the flickering frequency is, so that the warning effect in an emergency situation can be further improved.

In the above embodiment, although three threshold values as well as three durations and three flickering frequencies corresponding thereto are set, the present disclosure is not limited thereto. A curve of threshold values corresponding to durations and flickering frequencies may also be stored in the storage unit 3. The curve may satisfy that the lower the blood oxygen saturation is, the shorter the duration is, and the higher the flickering frequency is.

Furthermore, when it is judged that the blood oxygen saturation is lower than the first threshold value, counting the duration is started. If the blood oxygen saturation is lower than the second threshold value before the first duration is reached, it is preferable to continue counting the duration without recounting the duration. This can ensure that the user is alerted by a flickering display in time in a case where the blood oxygen saturation continuously decreases.

The oximeter 1 according to the present embodiment may further include an input unit 7, and at least one of the first threshold value, the second threshold value, the third threshold value, the first frequency, the second frequency, the third frequency, the first duration, the second duration, and the third duration is set by the input unit 7.

The input unit 7 is, for instance, a button. The button may be one or more elastic cylindrical buttons set in the casing and protruding from the surface of the casing. By pressing the button, the machine can be turned on and off, the function can be set, and the threshold values, frequencies, and durations can be set.

Furthermore, instead of setting the input unit 7, the input function may be set at the display unit 5. For instance, the display unit 5 has a touch control function, and the user implements the input control described above through the display unit 5.

Furthermore, the oximeter 1 according to the present embodiment may further include a wireless communication unit 8 that receives a parameter setting instruction from a mobile terminal and sends alarm information to the mobile terminal. The user can communicate with the wireless communication unit 8 through the mobile terminal, control the oximeter 1, or transmit the data detected by the oximeter 1 to the mobile terminal.

Furthermore, the oximeter 1 according to the present embodiment may further include a power supply unit 6. The battery unit 6 may be a dry battery or a rechargeable battery, and supplies power to various components of the oximeter 1.

Furthermore, the oximeter 1 according to the present embodiment may further include an I/O interface 9 which is, for instance, a USB interface. In a case where the battery unit 6 is a rechargeable battery, the battery unit 6 may be charged through the I/O interface 9.

Furthermore, the I/O interface 9 can be used as a collecting interface for externally connecting to other blood oxygen collecting devices 10, so that it can be connected to a traditional finger clip or finger sleeve blood oxygen collecting device, which is suitable for nighttime or long-term monitoring.

Furthermore, the display unit 6, in the case where the judging unit judges that the blood oxygen saturation is lower than the first threshold value, displays the blood oxygen saturation in a first font, and in the case where the judging unit judges that the blood oxygen saturation is lower than the second threshold value, displays the blood oxygen saturation in a second font greater than the first font. The display unit, in a case where the judging unit judges that the blood oxygen saturation is lower than the third threshold value, displays the blood oxygen saturation in a third font greater than the second font.

Furthermore, the display unit 6, in the case where the judging unit judges that the blood oxygen saturation is lower than the first threshold value, displays the blood oxygen saturation in a first brightness, and in the case where the judging unit judges that the blood oxygen saturation is lower than the second threshold value, displays the blood oxygen saturation in a second brightness greater than the first brightness. The display unit, in a case where the judging unit judges that the blood oxygen saturation is lower than the third threshold value, displays the blood oxygen saturation in a third brightness greater than the second brightness.

Specifically, the display font of the measurement parameters can be enlarged and displayed along with the levels; for instance, the size of the font can be changed from 12*12 pixels to 20*20 pixels, and further changed to 30*30 pixels. Along with the levels, different levels of backlight intensity are used, such as low brightness, medium brightness, and high brightness. The brightness can be changed by changing the power supply voltage of the display screen, and the voltage can be changed by connecting resistors with different resistance values in series or by PWM adjustment. To make it easier to see the flickering effect, small fonts and low brightness are used for the default display. This is to extend the life of the machine, and large font or high brightness is intended to attract attention. The font size and display levels of a backlight can be set.

Furthermore, in the case where the judging unit judges that the blood oxygen saturation is lower than the first threshold value, counting of the duration is started, and before the first duration is reached and in a case where the blood oxygen saturation is lower than a second threshold value, counting of the duration is continued.

Furthermore, the display unit 6, in the case where the judging unit judges that the blood oxygen saturation is lower than the first threshold value and it continues for the first duration, after further delaying a predetermined alarm duration, flickeringly displays the blood oxygen saturation at the first frequency.

Specifically, in order to further increase the stability of the alarm, judging of delaying the alarm duration is added. When the measured data exceeds the threshold value, the duration is counted, and when the corresponding duration is exceeded, an alarm is triggered after delaying the corresponding alarm duration.

Furthermore, the display unit 6 sets a flickering frequency, a display font, and/or a display brightness based on level of abnormality degree. The level of abnormality degree is graded based on the rate of change of the blood oxygen saturation or the number of exceeding the threshold values of the blood oxygen saturation.

The rate of change of the blood oxygen saturation is calculated based on the following Equation 1:

$$V_i = ((a-1)*(A_i - A_{i-1})/T + V_{i-1})/a \qquad \text{Equation 1}$$

where a is an adjustment coefficient, T is an overrun time, $V_i$ is the latest real-time rate of change, $V_{i-1}$ is the last real-time rate of change, $A_i$ is the latest measurement data, and $A_{i-1}$ is the last measurement data.

When the threshold values or/and the delay time ranges are too great due to improper setting by the user, it may not respond in time to a sharp deterioration. However, the sharp deterioration is worthy of attention, so dynamic change may be used to improve the reliability of the alarm.

The abnormality degree is actually the change speed, the rate of change or the number of exceeding the threshold values of data within the overrun time. The greater the change speed, the rate of change or the number of exceeding the threshold values is, the higher the abnormality degree is.

For instance, the change speeds of data are 2%/overrun time, 5%/overrun time, and 10%/overrun time, and correspond to the first, second, and third levels of abnormality degree, respectively. The rate of change is the difference between the latest measurement data and the last measurement data. There are positive rates of change and negative rates of change. A positive rate of change indicates that the latest value is greater than the last value, for example, when describing blood oxygen saturation, it indicates that the value is increasing. A negative rate of change indicates a decrease in value, and a decrease in value indicates a trend of deterioration. In order to avoid the influence of the fluctuation of the single data difference, the actually adopted rate of change is calculated using the above Equation 1, where a can be adjusted accordingly according to the collection frequency of data. For instance, when the collection frequency is 120 Hz, the value of a is 32. False alarms due to interference data can be avoided by using this Equation to calculate the actually adopted rate of change.

Furthermore, the number of exceeding the threshold values of the data measured within the overrun time is described as follows: when the measurement data exceeds a threshold value for the first time, the number is counted as 1. When the data falls back to the normal value, and then exceeds the threshold value again, the number is added with 1 and counted as 2. Accumulation is performed sequentially in the duration (where the measured data is not stable enough within the overrun time, and this mechanism is introduced in order to draw attention to data fluctuation).

When the abnormality degree exceeds a preset value, as the abnormality degree increases, the delay time becomes shorter, the threshold value range becomes smaller, and the frequency becomes higher. Conversely, as the abnormality degree becomes lower, the delay time becomes longer, the threshold value range becomes greater, and the frequency becomes lower.

Specifically, when the change speed exceeds a preset value, the greater the absolute value of the change speed is, the smaller the threshold value setting range and/or the shorter the delay time and/or the higher the frequency is, and otherwise the parameters will not be adjusted. Correspondingly, when the number of exceeding the threshold values exceeds a preset value, the greater the number is, the smaller the threshold value setting range and/or the shorter the delay time and/or the higher the frequency is, and otherwise the parameters will not be adjusted.

Furthermore, the delay time, for instance, at least one of the first duration, the second duration, and the third duration is calculated based on the following Equation 2:

$$T=((Ht-Lt)/(B-1)*A+Lt)/(B-A) \quad \text{Equation 2}$$

where A is measured data, B is a set threshold value, Ht is the maximum delay time, and Lt is the minimum delay time.

When the measured data is smaller than a low threshold value, the smaller the measured data (i.e., the greater the abnormality degree) is, the shorter the delay time is, and the higher the response rate is. If the measured data is A and the set threshold is B, the maximum value is B−1 when the measured data meets the alarm, which corresponds to the maximum delay time Ht. The minimum value of the measured data is 0, which corresponds to the minimum delay time Lt. The setting of the delay time takes into account the convenience of data processing and the requirements for processor processing capacity. As for the relationship between the data, the calculation amount of a linear function is relatively minimal. At the same time, the conditions for generating the alarm need to be added, and it is derived that the relationship between the measured data A and the delay time T is the above Equation 2, wherein the numerator is composed of a linear function determined by the set maximum delay time and the minimum delay time, while the denominator is obtained according to the minimum requirements for generating an alarm under actual conditions.

Furthermore, the display unit 6 further displays cumulative unprocessed alarm information.

After an alarm is generated, it can be turned off by medical staff. Or, if it is not effectively processed for a certain period of time and has returned to the normal value for a period of time, the alarm is turned off and a cumulative non-alarm reminder flag is added. The alarms under different threshold values are displayed separately, and the displaying can be numerical values, icons, etc. The flag is set to indicate that an alarm has occurred to draw attention, which can make it easier for medical staff to review the incident and guide care.

Although the oximeter according to the present disclosure has been described in detail through some exemplary embodiments, the above embodiments are not exhaustive. Those skilled in the art may implement various changes and modifications within the spirit and scope of the present invention. Therefore, the present disclosure is not limited to these embodiments, and the protection scope of the present disclosure is determined only by the appended claims.

What is claimed is:

1. An oximeter comprising:
   a blood oxygen collecting circuit that has a first light emitting circuit, a second light emitting circuit, and a light receiving sensor, the first light emitting circuit emitting a red light, the second light emitting circuit emitting an infrared light, and the light receiving sensor i) receiving the red light emitted by the first light emitting circuit and not absorbed by a human body and the infrared light emitted by the second light emitting circuit and not absorbed by the human body, and ii) converting them into an electrical signal;
   a storage circuit that stores a first threshold value and a second threshold value smaller than the first threshold value;
   a microprocessor that calculates a blood oxygen saturation of the human body based on the electrical signal detected by the light receiving sensor, and judges whether the blood oxygen saturation is lower than the first threshold value; and
   a display that, in a case where the microprocessor judges that the blood oxygen saturation is lower than the first threshold value, flickeringly displays the blood oxygen saturation at a first frequency and/or displays the blood oxygen saturation in a first brightness,
   wherein the microprocessor, in a case where it is judged that the blood oxygen saturation is lower than the first threshold value, judges whether the blood oxygen saturation is lower than the second threshold value,
   wherein the display, in a case where the microprocessor judges that the blood oxygen saturation is lower than the second threshold value, flickeringly displays the blood oxygen saturation at a second frequency greater than the first frequency and/or displays the blood oxygen saturation in a second brightness greater than the first brightness, wherein the display sets a flickering frequency, a display font, and/or a display brightness based on level of abnormality degree, wherein the level of abnormality degree is graded based on a rate of change of the blood oxygen saturation or a number of exceeding the threshold values of the blood oxygen saturation, and wherein the rate of change of the blood oxygen saturation is calculated based on the following Equation 1:

$$V_i=((a-1)*(A_i-A_{i-1})/T+V_{i-1})/a \qquad \text{Equation 1}$$

where a is an adjustment coefficient, T is an overrun time, $V_i$ is the latest real-time rate of change, $V_{i-1}$ is the last real-time rate of change, A is the latest measurement data, and $A_{i-1}$ is the last measurement data.

2. The oximeter according to claim 1, wherein the storage circuit further stores a third threshold value smaller than the second threshold value, wherein the microprocessor, in a case where it is judged that the blood oxygen saturation is lower than the second threshold value, judges whether the blood oxygen saturation is lower than the third threshold value, and wherein the display, in a case where the microprocessor judges that the blood oxygen saturation is lower than the third threshold value, flickeringly displays the blood oxygen saturation at a third frequency greater than the second frequency.

3. The oximeter according to claim 1, further comprising an input circuit for setting at least one of the first threshold value, the second threshold value, the first frequency, and the second frequency.

4. The oximeter according to claim 1, wherein the display further displays cumulative unprocessed alarm information.

5. The oximeter according to claim 1, further comprising a wireless communication circuit that receives a parameter setting instruction from a mobile terminal and sends alarm information to the mobile terminal.

6. The oximeter according to claim 1, wherein the oximeter is a finger clip oximeter, a wrist oximeter, or a head-mounted oximeter, wherein a blood oxygen collecting circuit of the finger clip oximeter comprises a concave blood oxygen collecting port in which a finger can be put, wherein the first light emitting circuit, the second light emitting circuit, and the light receiving sensor are set in the concave blood oxygen collecting port, wherein a blood oxygen collecting circuit of the wrist oximeter comprises a blood oxygen finger clip set outside a casing, and wherein the blood oxygen finger clip is connected with an interface set at the casing.

7. The oximeter according to claim 1, wherein the display, in the case where the microprocessor judges that the blood oxygen saturation is lower than the first threshold value, displays the blood oxygen saturation in a first font, and in the case where the microprocessor judges that the blood oxygen saturation is lower than the second threshold value, displays the blood oxygen saturation in a second font greater than the first font.

8. The oximeter according to claim 7, wherein the display, in a case where the microprocessor judges that the blood oxygen saturation is lower than a third threshold value smaller than the second threshold value, displays the blood oxygen saturation in a third font greater than the second font.

9. The oximeter according to claim 1, wherein the display, in a case where the microprocessor judges that the blood oxygen saturation is lower than a third threshold value smaller than the second threshold value, displays the blood oxygen saturation in a third brightness greater than the second brightness.

10. An oximeter, comprising:

a blood oxygen collecting circuit that has a first light emitting circuit, a second light emitting circuit, and a light receiving sensor, the first light emitting circuit emitting a red light, the second light emitting circuit emitting an infrared light, and the light receiving sensor receiving the red light emitted by the first light emitting circuit and not absorbed by a human body and the infrared light emitted by the second light emitting circuit and not absorbed by the human body, and converting them into an electrical signal;

a storage circuit that stores a first threshold value and a second threshold value smaller than the first threshold value;

a microprocessor that calculates a blood oxygen saturation of the human body based on the electrical signal detected by the light receiving sensor, and judges whether the blood oxygen saturation is lower than the first threshold value; and a display that, in a case where the microprocessor judges that the blood oxygen saturation is lower than the first threshold value, flickeringly displays the blood oxygen saturation at a first frequency and/or displays the blood oxygen saturation in a first brightness, wherein the microprocessor, in a case where it is judged that the blood oxygen saturation is lower than the first threshold value, judges whether the blood oxygen saturation is lower than the second threshold value, wherein the display, in a case where the microprocessor judges that the blood oxygen saturation is lower than the second threshold value, flickeringly displays the blood oxygen saturation at a second frequency greater than the first frequency and/or displays the blood oxygen saturation in a second brightness greater than the first brightness, wherein the storage circuit further stores a first duration, wherein the microprocessor, in a case where it is judged that the blood oxygen saturation is lower than the first threshold value, judges whether a duration in this case exceeds the first duration, and wherein the display, in a case where the microprocessor judges that the blood oxygen saturation is lower than the first threshold value and it continues for the first duration, flickeringly displays the blood oxygen saturation at the first frequency, at least one of the first duration, a second duration, and a third duration is calculated based on the following Equation 2:

$$T=((Ht-Lt)/(B-1)*A+Lt)/(B-A) \qquad \text{Equation 2}$$

where A is measured data, B is a set threshold value, Ht is the maximum delay time, and Lt is the minimum delay time.

11. The oximeter according to claim 10, wherein the storage circuit further stores a second duration smaller than or equal to the first duration, wherein the microprocessor, in a case where it is judged that the blood oxygen saturation is lower than the second threshold value, judges whether a duration in this case exceeds the second duration, and wherein the display, in a case where the microprocessor judges that the blood oxygen saturation is lower than the second threshold value and it continues for the second duration, flickeringly displays the blood oxygen saturation at the second frequency.

12. The oximeter according to claim 11, wherein the storage circuit further stores a third duration smaller than or equal to the second duration, wherein the microprocessor, in a case where it is judged that the blood oxygen saturation is lower than a third threshold value, judges whether a duration in this case exceeds the third duration, and wherein the display, in a case where the microprocessor judges that the blood oxygen saturation is lower than the third threshold value and it continues for the third duration, flickeringly displays the blood oxygen saturation at a third frequency.

13. The oximeter according to claim 10, wherein in the case where the microprocessor judges that the blood oxygen saturation is lower than the first threshold value, counting of the duration is started, and before the first duration is reached and in a case where the blood oxygen saturation is lower than a second threshold value, counting of the duration is continued.

14. The oximeter according to claim 10, wherein the display, in the case where the microprocessor judges that the blood oxygen saturation is lower than the first threshold value and it continues for the first duration, after further delaying a predetermined alarm duration, flickeringly displays the blood oxygen saturation at the first frequency.

* * * * *